(12) United States Patent
Cronin et al.

(10) Patent No.: US 8,591,526 B2
(45) Date of Patent: Nov. 26, 2013

(54) ENDOSURGERY SUTURING DEVICE

(75) Inventors: James Cronin, Greenville, SC (US);
Mary Frecker, State College, PA (US);
Abraham Mathew, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 621 days.

(21) Appl. No.: 12/442,007

(22) PCT Filed: Nov. 2, 2007

(86) PCT No.: PCT/US2007/083472
§ 371 (c)(1),
(2), (4) Date: Mar. 19, 2009

(87) PCT Pub. No.: WO2008/058005
PCT Pub. Date: May 15, 2008

(65) Prior Publication Data
US 2010/0049219 A1    Feb. 25, 2010

Related U.S. Application Data

(60) Provisional application No. 60/864,197, filed on Nov. 3, 2006.

(51) Int. Cl.
*A61B 17/04* (2006.01)
*A61B 17/12* (2006.01)

(52) U.S. Cl.
USPC ............................ 606/144; 606/207; 606/223

(58) Field of Classification Search
USPC .......... 606/139, 144–148, 205–211, 222–227
See application file for complete search history.

(56) References Cited

U.S. PATENT DOCUMENTS

| | | | |
|---|---|---|---|
| 5,181,919 A | 1/1993 | Bergman et al. | |
| 5,478,344 A * | 12/1995 | Stone et al. | 606/144 |
| 5,573,543 A | 11/1996 | Akopov et al. | |
| 5,741,277 A | 4/1998 | Gordon et al. | |
| 5,984,939 A * | 11/1999 | Yoon | 606/170 |
| 6,719,763 B2 | 4/2004 | Chung et al. | |
| 6,755,843 B2 | 6/2004 | Chung et al. | |

(Continued)

OTHER PUBLICATIONS

Powell, K.M., "Design of Multifunctional Surgical Tools Including a Method for Designing a Nonlinear Static Balance Mechanism," Masters Thesis, Mechanical & Nuclear Engineering, Penn State University, University Park, PA (2005).

(Continued)

*Primary Examiner* — Thomas McEvoy
(74) *Attorney, Agent, or Firm* — Gifford, Krass, Sprinkle, Anderson & Citkowski, P.C.; Douglas L. Wathen (57) ABSTRACT

A suturing device includes an elongated sheath and a suturing assembly. The elongated sheath has a working end for insertion through a working channel in an endoscope and has an inner passage. The suturing assembly includes an elongated flexible base member, a first suturing arm and a second suturing arm. The suturing arms each have a proximal end interconnected with the elongated base member and an opposite distal end. A needle receiver is disposed at the distal end of each suturing arm. The suturing arms are movable between an open position wherein the distal ends are spaced apart by a first distance and a closed position wherein the distal ends are spaced apart by a second distance less than the first distance.

15 Claims, 11 Drawing Sheets

(56) References Cited

U.S. PATENT DOCUMENTS

| | | |
|---|---|---|
| 6,997,931 B2 | 2/2006 | Sauer et al. |
| 2003/0065338 A1 | 4/2003 | Takamoto et al. |
| 2003/0216613 A1 | 11/2003 | Suzuki et al. |
| 2005/0021061 A1 * | 1/2005 | Dennis .......................... 606/157 |
| 2005/0075653 A1 | 4/2005 | Saadat et al. |

OTHER PUBLICATIONS

Hu, Bing, Chung, S.C. Sydney, Sun, Lawrence C.L., Kawashima, Koichi, Yamamoto, Tetsuya, Cotton, Peter B., Gostout, Christopher J., Hawes, Robert H., Kalloo, Anthony N., Kantsevoy, Sergey V Pasricha, Pankaj, J., "Eagle Claw II: a novel endosuture device that uses a curved needle for major arterial bleeding: a bench study," Gastrointestinal Endoscopy, vol. 62, No. 2, 2005, p. 266-270.

Hu, Bing, Chung, S.C. Sydney, Sun, Lawrence C.L., Lau, James Y.W,, Kawashima, Koichi, Yamamoto, Tetsuya, Cotton, Peter B., Gostout, Christopher J., Hawes, Robert H., Kalloo, Anthony N., Kantsevoy, Sergey V., Pasricha, Pankaj J, "Endoscopic suturing without extracorporeal knots: a laboratory study," Gastrointestinal Endoscopy, vol. 62, No. 2, 2005, p. 230-233.

Frecker, M.I,, Dziedzic, R.P., Haluck, R.S., "Design of multifunctional compliant mechanism for minimally invasive surgery," Min. Invas, Ther & Allied Technol, 2002: 11(5/6) 311-319.

Frecker, Mary I., Powell, Katherine M., Haluck, Randy, "Design of a Multifunctional Compliant Instrument for Minimally Invasive Surgery," Transactions of the ASME, vol. 127, Nov. 2005, p. 990-993.

Awan, Amjad N., Swain, C.P., "Endoscopic vertical band gastroplasty with an endoscopic sewing machine," Gastrointestinal Endoscopy, vol. 55, iss. 2, 2002, p. 254-256.

* cited by examiner

ENDOSURGERY SUTURING DEVICE

REFERENCE TO RELATED APPLICATION

This application claims priority to U.S. Provisional Patent Application Ser. No. 60/864,197, filed Nov. 3, 2006, the entire content of which is incorporated by reference.

FIELD OF THE INVENTION

The present invention relates generally to suturing devices and methods and, more specifically, to a suturing device for use through an endoscope.

BACKGROUND OF THE INVENTION

Traditionally, gastrointestinal endoscopy is mostly a diagnostic procedure where a flexible scope is passed into the stomach or the intestine. However, there is growing interest in the execution of surgical procedures via flexible endoscopes inserted through natural orifices as an alternative to the use of percutaneous laparoscopic instruments. This paradigm shift is being called natural orifice transluminal endoscopic surgery (NOTES). In NOTES procedures, the endoscope is passed through the esophagus and an incision made in the stomach to obtain access to the abdominal cavity. Transgastric access to the abdominal cavity opens a new window for treatment and may be especially beneficial for patients at increased operative risk.

In a handful of academic centers, skilled interventional gastroenterologists and laparoscopic surgeons are collaborating to develop the field of NOTES. Although only a few preliminary experiments using animal models have been published, these studies demonstrate the feasibility and safety of transluminal approach to the peritoneal cavity with long-term survival. The first report published by Kalloo et al. demonstrated the feasibility and safety of the per oral transgastric endoscopic approach. Other transgastric peritoneal procedures in porcine models have been reported including tubal ligation, cholecystectomy, gastrojejunostomy, splenectomy, and oophorectomy with tubectomy. An appendectomy has been performed in a human patient.

NOTES has been the subject of several recent editorials including one calling flexible endoscopic surgery the 'coming revolution' in gastrointestinal procedures. The authors contend that the laparoscopic revolution is over and that the next great change in surgery lies in new technology that will allow progressively more aggressive interventions via a natural body orifice. They cite the need for new, flexible instrumentation that will enable surgeons to perform many surgical tasks efficiently. However, rapid progress in this field has been hindered by the lack of adequate instruments that are specifically geared towards performing endoscopic surgery. Most available instruments are mere extended versions of conventional open instruments; open/close handle movements are translated through a slender extension tube to a simple, single degree of freedom effector at the instrument tip. The surgeon's ability to complete more complex procedures is limited by the requisite straight-line access, limited movements of the instrument tip, and the need to exchange instruments to perform different tasks.

SUMMARY OF THE INVENTION

According to a first embodiment of the present invention, a suturing device provided for suturing with a suturing needle having a first end and a second end. The suturing device includes an elongated sheath and a suturing assembly. The elongated sheath has a working end for insertion through a working channel in an endoscope. The elongated sheath has an inner passage defined through at least a portion of the sheath adjacent the working end.

The suturing assembly includes an elongated flexible base member having a working end and a handle end. A first suturing arm has a proximal end interconnected with the working end of the elongated base member and an opposite distal end. A first needle receiver is disposed at the distal end of the first suturing arm. A second suturing arm has a proximal end interconnected with the working end of the elongated base member and an opposite distal end. A second needle receiver is disposed at the distal end of the second suturing arm. The suturing arms are movable between an open position wherein the distal ends are spaced apart by a first distance and a closed position wherein the distal ends are spaced apart by a second distance less than the first distance. In some embodiments the first and second suturing arms are formed of a flexible and resilient material such that moving the arms between the open and closed positions flexes the suturing arms, and the suturing arms being biased towards the open position.

The suturing assembly is disposed through the inner passage of the sheath. The sheath is movable relative to the suturing assembly between a retracted position and an extended position. In the extended position, the sheath engages the suturing arms and urges the suturing arms towards the closed position.

The suturing device may further include a first needle locking element interacting with the first needle receiver to selectively lock the suturing needle in the first needle receiver and a second needle locking element interacting with the second needle receiver to selectively lock the suturing needle in the second needle receiver.

In some versions, the suturing needle has a flattened portion adjacent the first end and another flattened portion adjacent the second end and the needle locking elements engage the flattened portions to selectively lock the suturing needle in one of the needle receivers.

The suturing needle may have a pair of opposed flattened areas adjacent each of the first and second ends and the needle locking elements may each have a forked end, the forked end engaging one of the pairs of opposed flattened areas to selectively lock the suturing needle in one of the needle receivers.

In some versions, each needle locking element has an elongated flexible base portion disposed adjacent the flexible base member and a working portion disposed adjacent the suturing arms. Further, each needle-locking element may have a forked end disposed in one of the needle receivers.

In further versions, each suturing arm has a base segment and a working segment, the base segment extending from the proximal end to a transition region and the working segment extending from the transition region to the distal end. In this version, the base segments are generally parallel when the suturing arms are in the open position. In this version the base segments of the suturing arms may be generally disposed in the inner passage of the sheath when the sheath is in the retracted position, and at least a portion of the working segments of the suturing arms may be disposed in the inner passage of the sheath when the sheath is in the extended position. Further, the working segments of the suturing arms may be angled outwardly when the suturing arms are in the open position.

In certain versions, the base segment of one of the suturing arms has a longitudinal slot disposed therethrough, and the base segment of the other suturing arm is at least partially disposed in the slot when the suturing arms are flexed into the closed position.

The further versions, the transition regions of the suturing arms are moved into contact when the suturing arms are flexed from the open position to the closed position, thereby reducing the stress in the flexible and resilient material forming the arms.

The suturing device may be used in combination with an inventive suturing needle. This suturing needle has a needle body extending between a first pointed end and a second pointed end. The needle body has a flattened portion defined adjacent each of the first and second ends and a suture receiving slot defined in the body. A further inventive suturing needle has a generally planar needle body with a first pointed end, an opposed second pointed end and a midportion extending therebetween. The needle body has an elongated suture receiving slot extending from one of the pointed ends into the midportion of the needle body. This needle may have a pair of generally planar faces with a perimeter edge interconnecting the planar faces, with a notch defined in the perimeter edge adjacent each of the pointed ends.

The present invention also provides for a method of suturing thru an endoscope. According to the method, an endoscope is provided with working channel defined therethrough. A suturing needle is provided having a first end and a second end. A suturing device is provided, wherein the suturing device includes an elongated sheath and a suturing assembly. The elongated sheath has a working end for insertion through the working channel in the endoscope and has an inner passage defined through at least a portion of the sheath adjacent the working end. The suturing assembly includes an elongated flexible base member with a working end and a handle end. A first suturing arm has a proximal end interconnected with the working end of the elongated base member and an opposite distal end. A first needle receiver is disposed at the distal end of the first suturing arm. A second suturing arm has a proximal end interconnected with the working end of the elongated base member and an opposite distal end. A second needle receiver is disposed at the distal end of the second suturing arm. The suturing arms are movable between an open position wherein the distal ends are spaced apart by a first distance and a closed position wherein the distal ends are spaced apart by a second distance less than the first distance. The first and second suturing arms are formed of a flexible and resilient material such that moving the arms between the open and closed positions flexes the suturing arms, and the suturing arms are biased towards the open position. The suturing assembly is disposed through the inner passage of the sheath. The sheath is movable relative to the suturing assembly between a retracted position and an extended position. In the extended position, the sheath engages the suturing arms and urges the suturing arms towards the closed position.

According to the method, the suturing device is disposed thru the working channel of the endoscope, one end of the suturing needle is positioned in one of the needle receivers, and suturing is performed using the suturing needle and the suturing device.

DETAILED DESCRIPTION OF THE PREFERRED EMBODIMENTS

Figure 1:
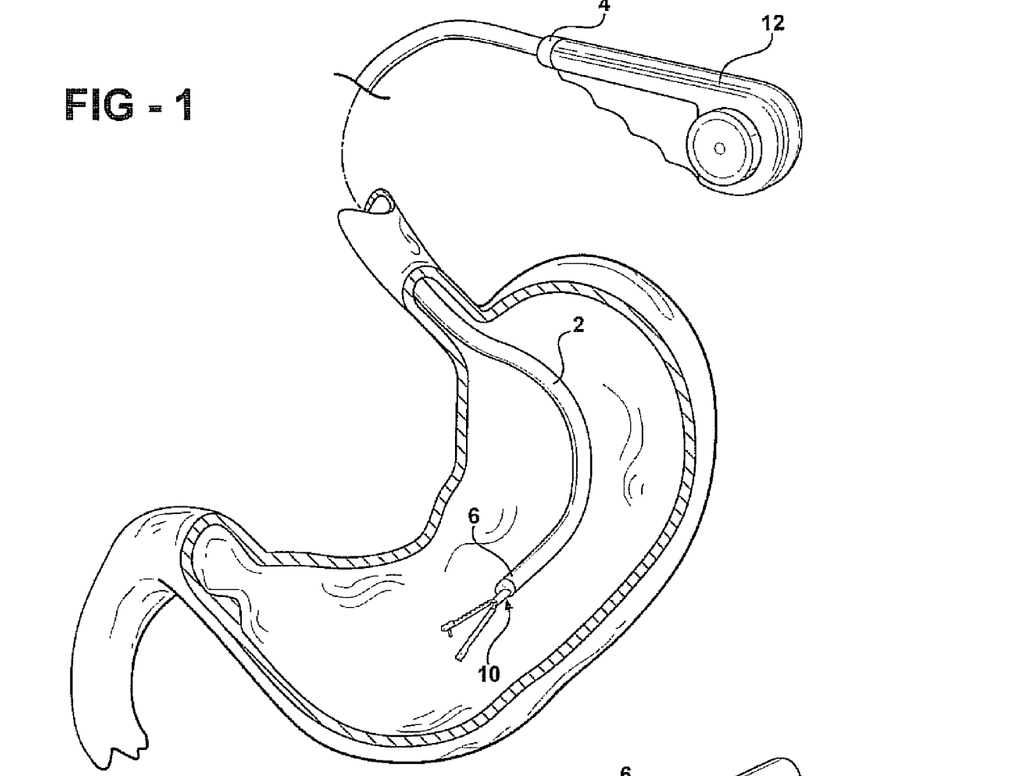
FIG. 1 is a perspective view of a suturing device according to an embodiment of the present invention disposed through an endoscope, with the endoscope extending into a stomach.

The present invention is targeted at incisionless surgery using rigid or flexible endoscopes. An endoscope has several channels including light transmission, image transmission, air and water, plus one or more "working channels" through which instruments are inserted. An example flexible endoscope is shown in FIG. 1. Traditionally, gastrointestinal endoscopy is mostly a diagnostic procedure where a flexible endoscope is passed into the stomach or the intestine, as shown. However, there is growing interest in the execution of surgical procedures via flexible endoscopes inserted through natural orifices as an alternative to the use of percutaneous laparoscopic instruments. This paradigm shift is being called natural orifice transluminal endoscopic surgery (NOTES). In NOTES procedures, the endoscope is passed through the esophagus and an incision made in the stomach to obtain access to the abdominal cavity, thus avoiding an external wound and a deeper dissection. Transgastric access to the abdominal cavity opens a new window for treatment and may be especially beneficial for patients at increased operative risk.

One of the main challenges in flexible endoscopic surgery is reported to be the development of suturing and anastomatic devices. Embodiments of the present invention include a suturing device that can be used in endoscopic surgery. While the present invention may be used through a working channel of an endoscope in NOTES procedures, those of skill will recognize that the present invention is not limited to use with an endoscope or to NOTES procedures. It may also be used "piggybacked" on a scope or by itself and is not limited to specific procedures.

Referring again to FIG. 1, the endoscope itself is indicated at 2. The endoscope extends between two ends 4 and 6 with the end 6 inserted into the body. A detailed view of the end 6 is provided in FIG. 2. As shown, the endoscope has a working channel 8 defined therethrough. Typically, this channel has a diameter in the range of 3 to 6 mm.

Figure 2:
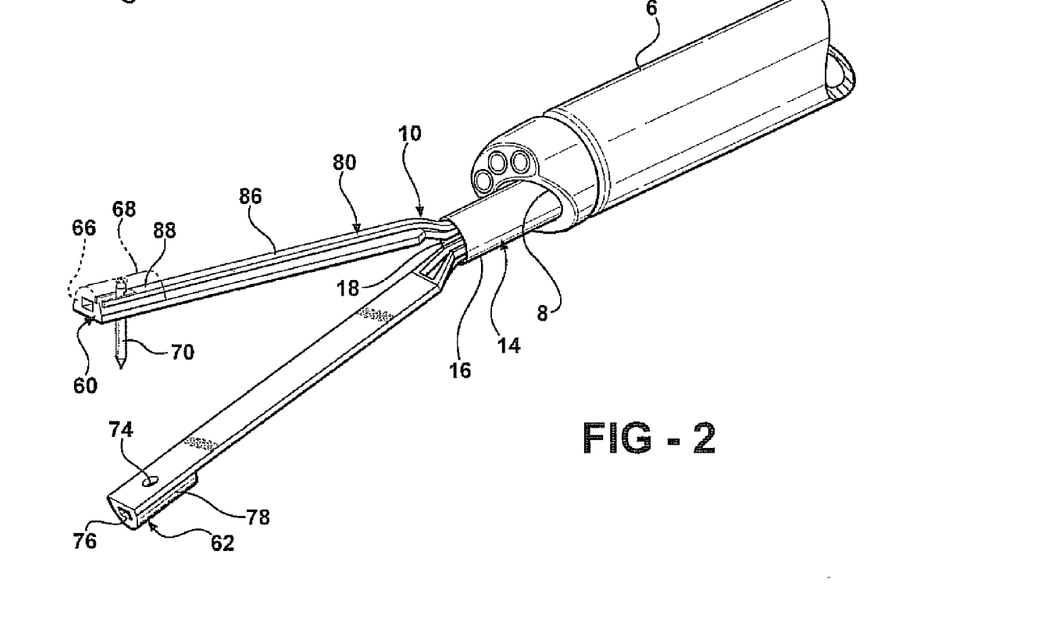
FIG. 2 is a perspective view of one end of a suturing device according to an embodiment of the present invention extending from the end of an endoscope, with the suturing arms of the suturing device in the open position.

A suturing device according to the present invention is indicated at 10 in FIGS. 1 and 2. When used with an endoscope, the suturing device 10 is disposed through the working channel 8 such that the working end of the suturing device extends from the end 6 of the endoscope. The suturing device 10 has a one end adjacent the end 4 of the endoscope and may be interconnected with a handle or control, such as shown at 12.

Figure 4:
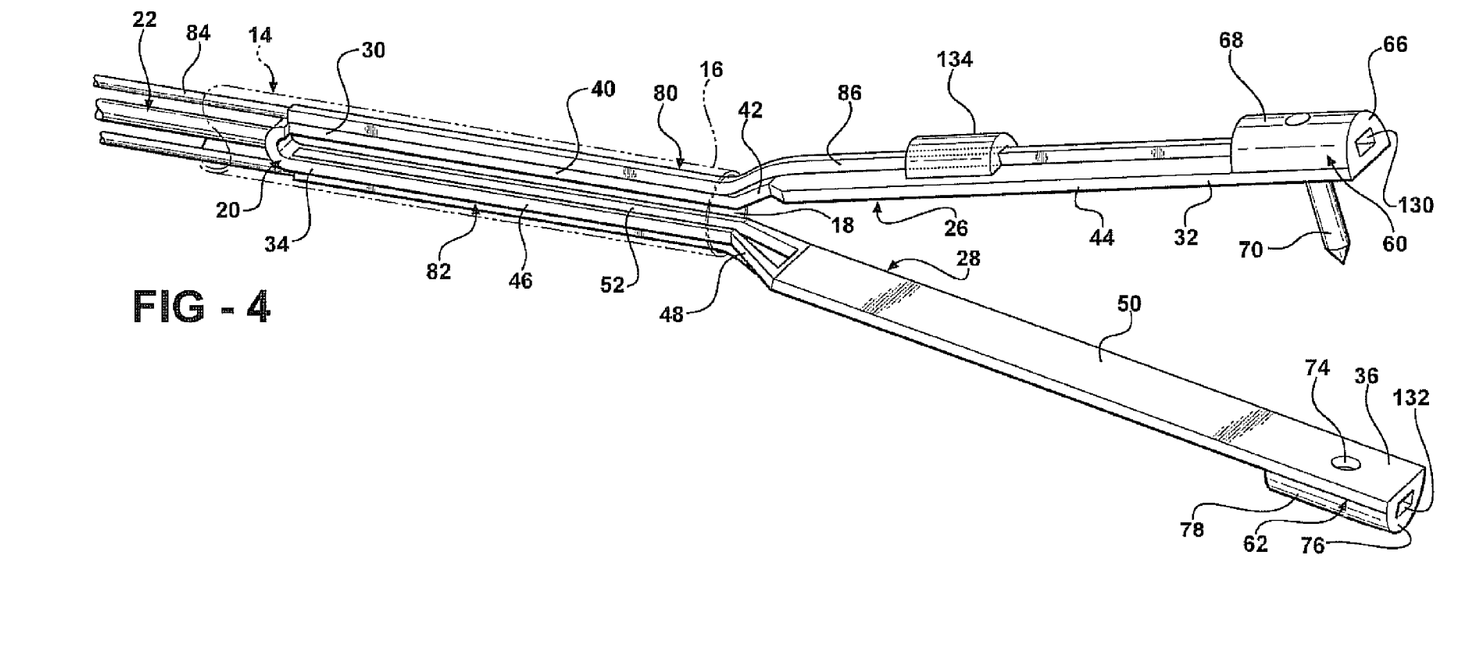
FIG. 4 is a perspective view of one end of a suturing device according to an embodiment of the present invention with the suturing arms in the open position and a needle engaging one of the needle receivers.

The suturing device according to the present invention may take a variety of forms, with the working end of one embodiment illustrated in more detail in FIG. 4. The suturing device includes an elongated sheath 14 having a working end 16 that is inserted through the working channel of the endoscope. The sheath 14 in this embodiment is tubular with a consistent circular cross section between its ends, though it may take other forms. In order to fit through the working channel of a typical endoscope, it is preferred that the sheath have an outer diameter of less than or equal to approximately 6 mm. The sheath 14 has an inner passage 18 defined through at least a portion of the sheath adjacent the working end 16. In the illustrated embodiment, the inner passage 18 would extend the entire length of the sheath 14.

The suturing device 10 also includes a suturing assembly 20 which is disposed through the inner passage 18 of the sheath 14. Referring to FIG. 4, the suturing assembly 20 includes an elongated flexible base member 22 having a handle end and a working end 24. The handle end in some embodiments extends to the end 4 of the endoscope and is used to manipulate the suturing assembly 20. The suturing assembly 20 further includes a first suturing arm 26 and a second suturing arm 28. The first suturing arm 26 has a proximal end 30 interconnected with the working end 24 of the base member 22 and an opposite distal end 32. Likewise, the second suturing arm 28 has a proximal end 34 interconnected with the working end 24 of the base member 22 and an opposite distal end 36. The two suturing arms 26 and 28 are similar and generally symmetrical, but may be shaped somewhat differently.

Figure 5:
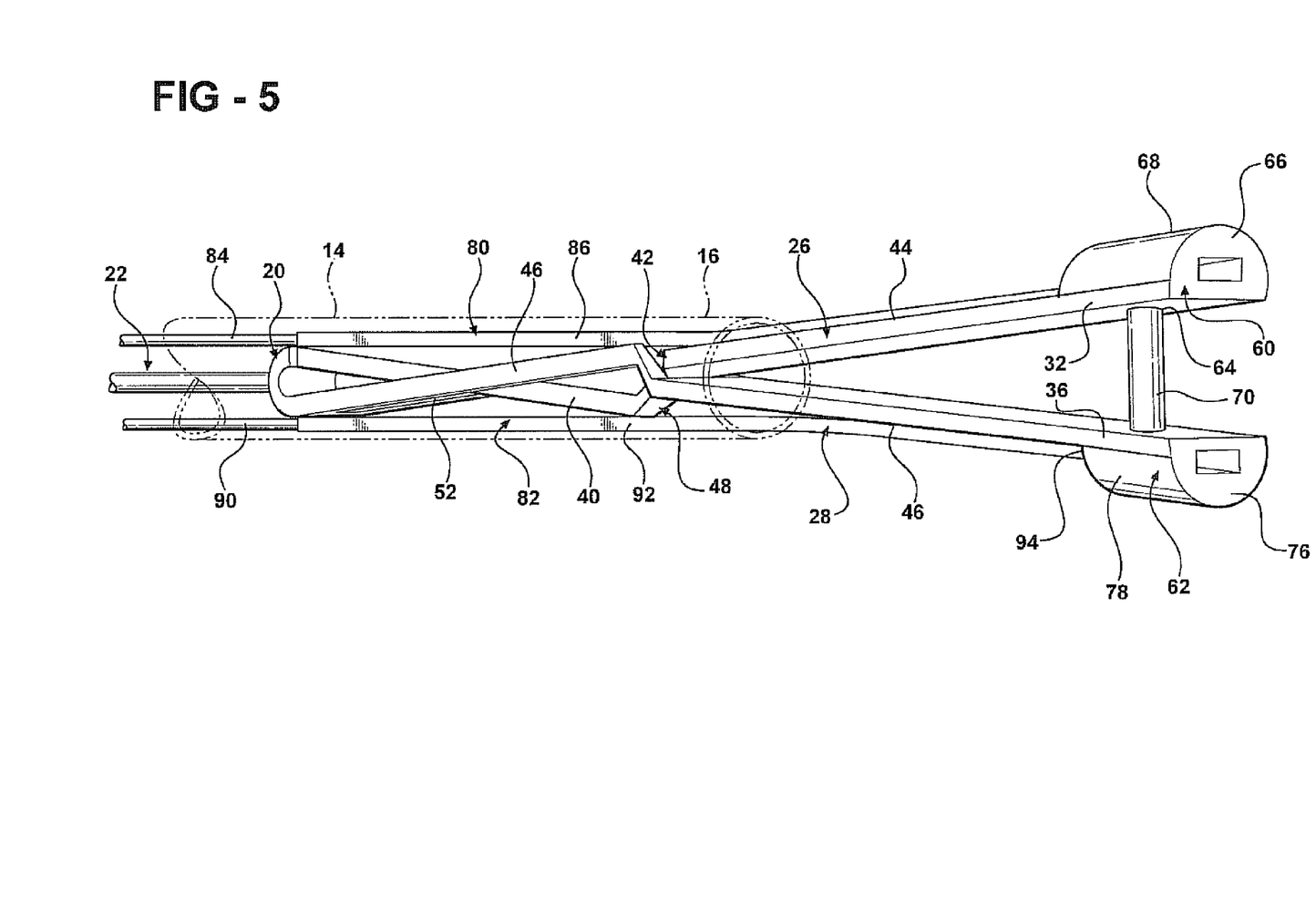
FIG. 5 is a perspective view of the suturing device of FIG. 4 with the working end of the sheath moved to an extended position so as to flex the suturing arms into a closed position and with a suturing needle engaging the needle receivers at the distal end of both suturing arms.

The arms 26 and 28 are movable between an open position, shown in FIG. 4, and a closed position, shown in FIG. 5. In the open position of FIG. 4, the distal ends 32 and 36 of the arms 26 and 28 are spaced apart by a first distance. In the closed position of FIG. 5, the distal ends 32 and 36 are separated by a second distance that is less than the first distance. In preferred embodiments, the suturing arms 26 and 28 are formed of a flexible and resilient material such that the arms flex when moved from the open position to the closed position. In the illustrated embodiment, the arms 26 and 28 are formed such that they are biased towards the open position due to the resiliency of the material.

In order to move the suturing arms from the open position to the closed position, the sheath 14 is moved from a retracted position, shown in FIG. 4, to an extended position, shown in FIG. 5. As shown, as the sheath 14 is moved towards the extended position, which is towards the distal ends 32 and 36 of the arms 26 and 28, the arms are urged towards one another.

The suturing arms 26 and 28 may take a variety of forms. In the embodiment illustrated in FIGS. 4 and 5, the first suturing arm 26 may be said to have a base segment 40 that extends from the proximal end 30 to a transition region 42 and a working segment 44 extending from the transition region 42 to the distal end 32. Likewise, the second suturing arm 28 may be said to have a base segment 46 that extends from the proximal end 34 to a transition region 48 and a working segment 50 extending from the transition region 48 to the distal end 36. When the sheath 14 is in the retracted position, as shown in FIG. 4, the base segments 40 and 46 of the arms 26 and 28 are generally disposed in the inner passage 18 of the sheath 14 and are generally parallel to each other. At the transition regions 42 and 48 the arms transition from the generally parallel base segments 40 and 46 to the outwardly angled working segments 44 and 50. As the sheath 14 is moved to the extended position of FIG. 5, the working end 16 of the sheath extends over at least a portion of the working segments 44 and 50 of the arms thereby urging them towards one another.

In the embodiment illustrated in FIGS. 4 and 5, the base segment 46 of one of the arms has a longitudinal slot 52 defined therethrough while the base segment 40 of the other arm is narrower and shaped to be received in the slot when the arms flex towards one another. This condition is illustrated in FIG. 5, where the base segment 40 is at least partially disposed in the slot 52 in the base segment 46. This overlap or intertwining of the arms allows for improved movement between the open and closed positions. As will be clear to those of skill in the art, an important design constraint in a flexible device is the stress level in the material. If the stress level is too high for the material used, failure will occur. In some embodiments of the present invention, stress relief is provided due to contact between the arms at the transition regions. In the embodiment of FIG. 5, it can be seen that the arms are in contact at the transition regions 42 and 48 when the arms are urged to the closed position. As will be clear to those of skill in the art, this contact reduces the maximum stress in the material. While contact is not required in all embodiments, it is a preferred feature.

Figure 7:
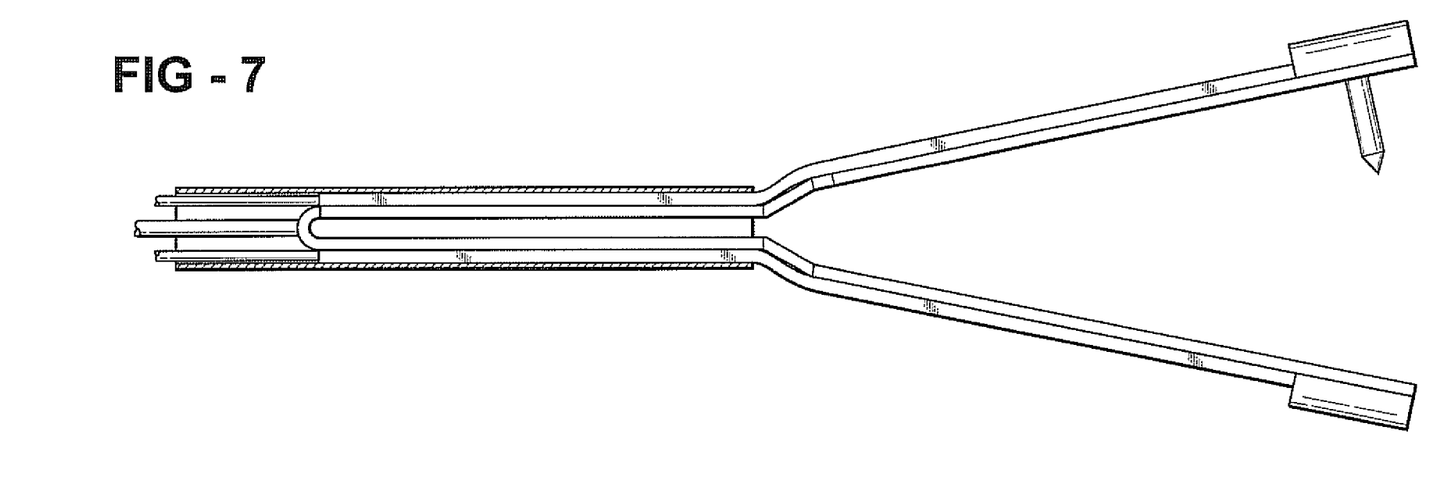
FIG. 7 is a side elevational view of the suturing device of FIGS. 4-6 with the suturing arms in the open position.
Figure 8:
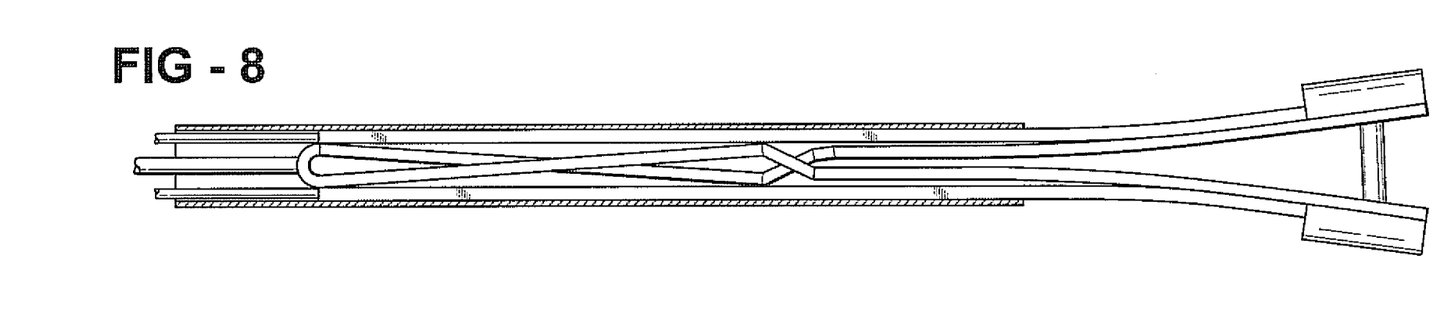
FIG. 8 is a side elevational view of the suturing device of FIGS. 4-7 with the suturing arms in the closed position.

FIGS. 7 and 8 provide further views of the suturing assembly with the suturing arms shown in the open position in FIG. 7 and the closed position in FIG. 8.

Referring again to FIGS. 2, 4 and 5, the first suturing arm 26 has a first needle receiver 60 disposed at the distal end 32 and the second suturing arm 28 has a second needle receiver 62 disposed at the distal end 36. In the illustrated embodiment, the needle receiver 60 includes an opening 64 in the inner face of the first suturing arm 26 and a housing 66 on the outer face. The housing has an arcuate outer surface 68. In FIGS. 2 and 4, a suturing needle 70 has one end received in the first needle receiver 60. The second needle receiver 62 includes an opening 74 in the inner face of the second suturing arm 28 and a housing 76 with an arcuate outer surface 78 on the outer face of the arm 28. When the suturing arms 26 and 28 are urged into the closed position, as shown in FIG. 5, the suturing needle 70 has its ends received in both needle receivers 60 and 62. As will be clear to those of skill in the art, during use of the suturing device, if tissue is positioned between the distal ends 32 and 36 of the arms 26 and 28, and the arms are moved to the closed position, the needle 70 will pass thru the tissue.

In some embodiments, the ends of the needle 70 are allowed to penetrate into the needle receivers only a limited distance, thereby limiting how close the distal ends 32 and 36 can be. In other embodiments, the needle may be allowed to travel farther.

Figure 6:
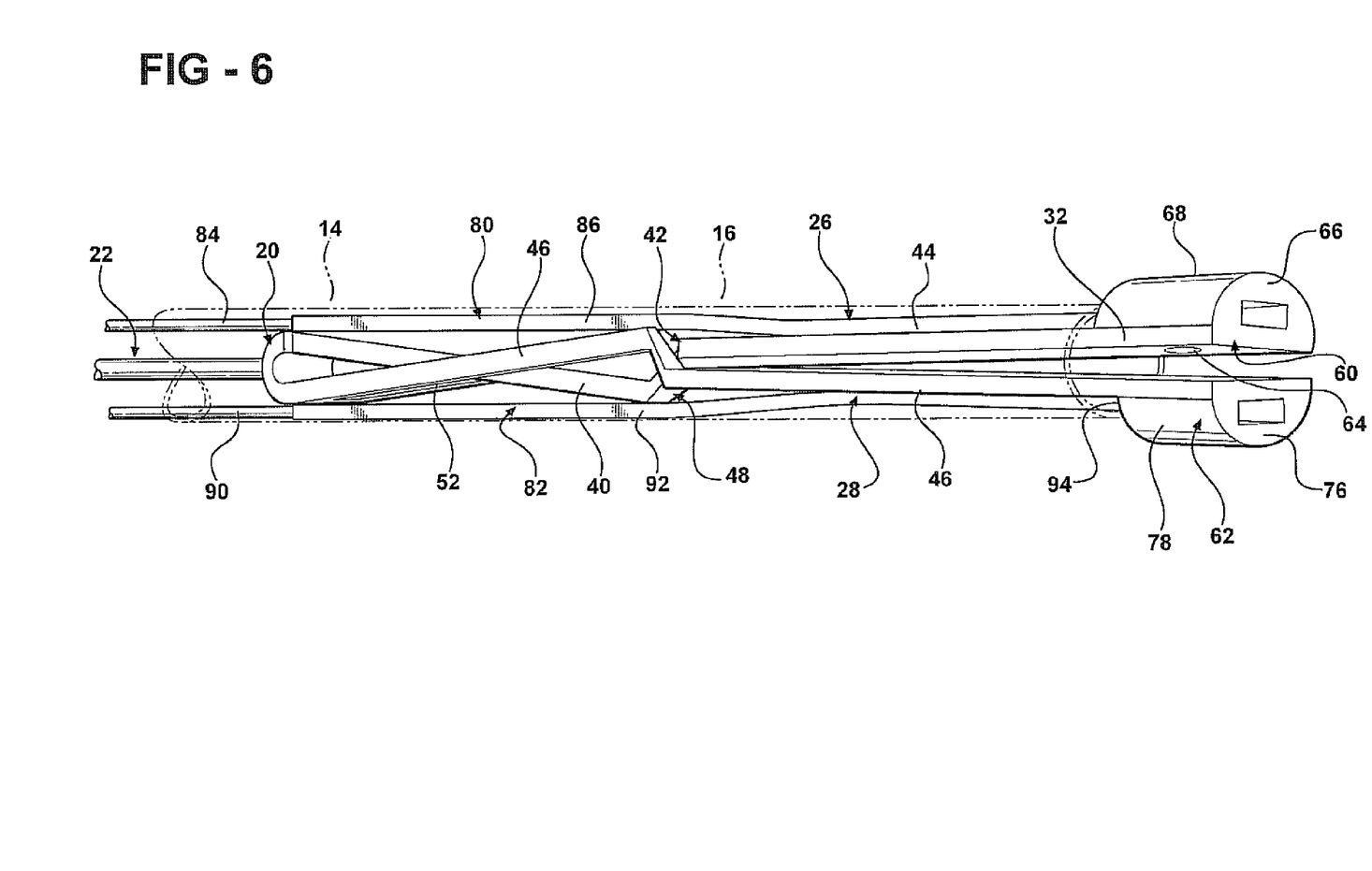
FIG. 6 is a perspective view of the suturing device of FIGS. 4 and 5 with the suturing needle removed and the suturing arms retracted into the sheath.

If the needle 70 is removed from both needle receivers, the distal ends 32 and 36 of the arms 26 and 26 may move farther toward one another and the suturing device may be retracted partially or completely into the sheath 14, as shown in FIG. 6. This allows the suturing device to be inserted through an endoscope since the sheath 14 is sized to pass through the working channel of the endoscope.

Figure 13:
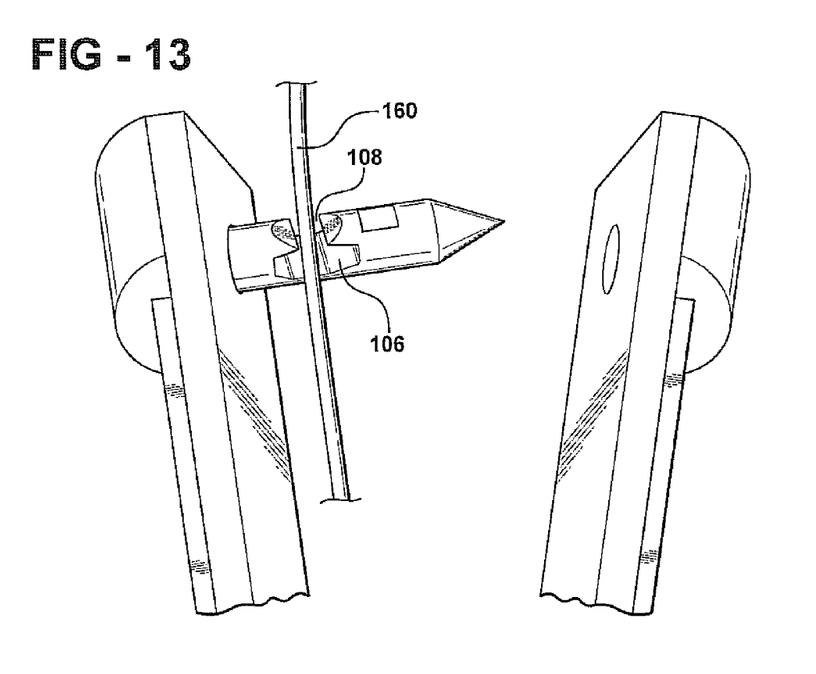
FIG. 13 is a perspective view of the distal ends of two suturing arms with a suturing needle received in one needle receiver and suturing material being received in a suture receiving slot in the needle body.
Figure 14:
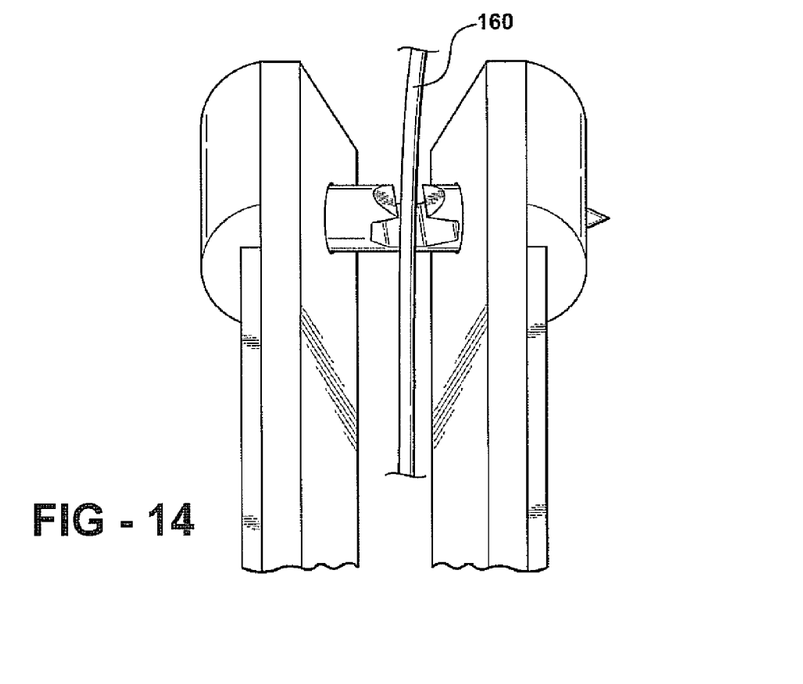
FIG. 14 is a perspective view similar to FIG. 13 but with the suturing arms moved to the closed position and both ends of the suturing needle disposed in the needle receivers.
Figure 15:
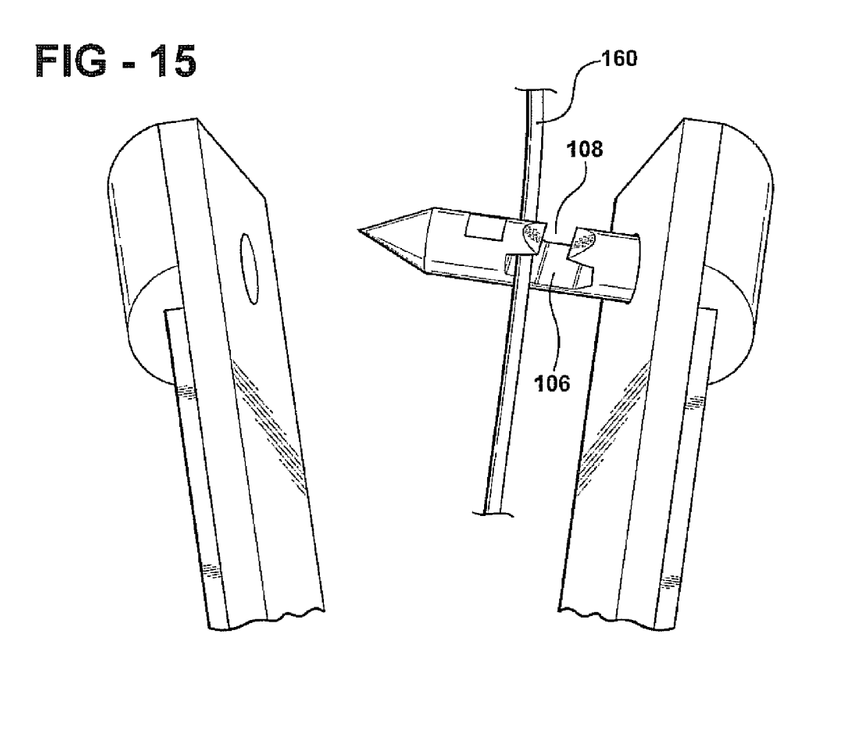
FIG. 15 is a perspective view similar to FIGS. 13 and 14 with the suturing arms returned to an open position and the suturing needle received in the other needle receiver.

As will be clear to those of skill in the art, it is preferred that the suturing device include the ability to selectively secure one end of the suturing needle in one of the needle receivers. When the needle pierces tissue, the tissue will tend to grip the needle and positive retention is required to maintain the needle in one of the receivers. In preferred embodiments of the present invention, one end of the needle may be secured in one of the needle receivers as shown in FIG. 13. The suturing arms may then be moved to the closed position as shown in FIG. 14 and the needle may be secured in the other needle receiver and released from the first needle receiver. When the suturing arms are returned to the open position as shown in FIG. 15, the needle is then retained in the other receiver allowing suturing to be performed. The procedure may be repeated to move the needle from one arm to the other to perform various suturing steps.

In the embodiment of the present invention illustrated in FIGS. 2, 4 and 5, the suturing device 10 further includes a first needle locking element 80 interacting with the first needle receiver 60 for selectively locking the suturing needle 70 in the first needle receiver 60. Similarly, a second needle locking element 82 is provided and interacts with the second needle receiver 62 for selectively locking the suturing needle 70 in the second needle receiver. The needle locking elements may take a variety of forms. In the illustrated embodiment, the first needle locking element 80 has an elongated flexible base portion 84 which extends adjacent the flexible base member 22 and a working portion 86 that is disposed adjacent the first suturing arm 26. The first needle locking element 80 has a working end 88 that engages the end of the suturing needle 70. Similarly, the second needle locking element 82 has an elongated flexible base portion 90 which extends adjacent the flexible base member 22 and a working portion 92 that is disposed adjacent the second suturing arm 28 and terminates in a working end 94.

Figure 11:
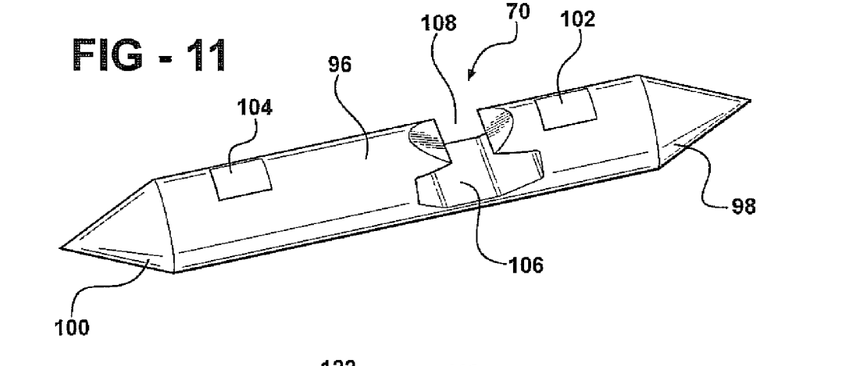
FIG. 11 is a perspective view of an embodiment of a suturing needle that may form part of the present invention.
Figure 16:
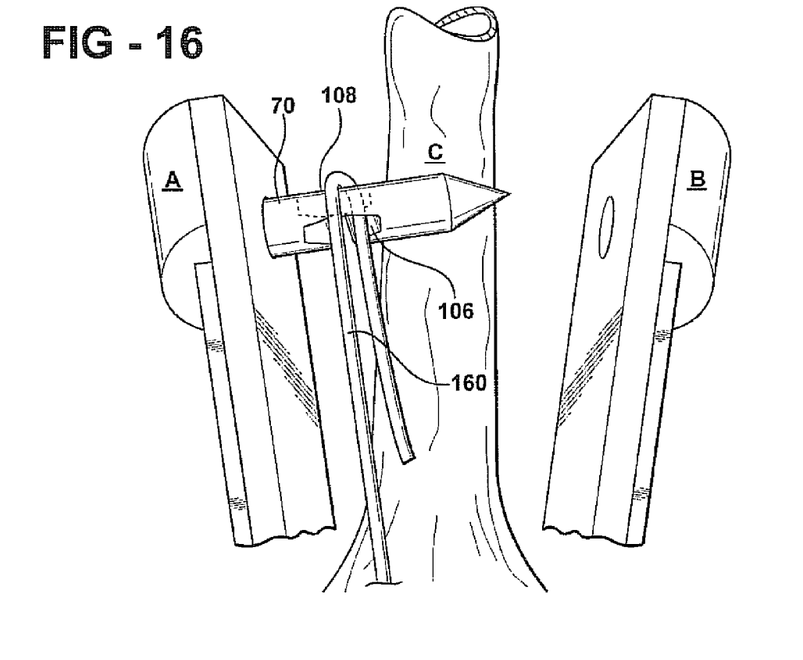
FIGS. 16-21 are a series of perspective views of two suturing arms, a suturing needle, and suturing material illustrating use of the present invention to tie a knot about a piece of tissue.

The design of the needle locking elements depends on the design of the needle. Referring to FIG. 11, one embodiment of the suturing needle 70 is illustrated in more detail. The suturing needle 70 has a needle body 96 which extends between a first pointed end 98 and a second pointed end 100. Flattened areas 102 and 104 are defined in the outer surface of the needle body 96 adjacent the ends 98 and 100, respectively. In some embodiments, the flattened areas have corresponding flattened areas on the other side of the body such that the flattened areas are provided in opposed pairs. A suture receiving slot 106 is defined in the needle body 96 between the ends. As shown, the suture receiving slot has a narrow opening 108 that opens into a larger slot. This allows threading or rethreading of the needle 70. The suturing material can be "caught" by the opening 108 to place the suturing material into the slot 106. FIG. 13 illustrates a piece of suturing material 160 being received through the narrow opening 108 into the suture receiving slot 106. As shown in FIG. 16, the suturing material 160 may move away from the opening 108 and deeper into the slot 106.

Figure 3:
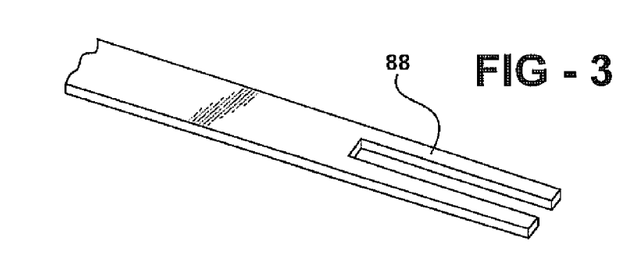
FIG. 3 is a perspective view of the working end of one version of a needle locking element for use with the present invention.

For the embodiment of the suturing needle 70 with pairs of opposed flattened areas adjacent each end, the working ends 88 and 94 of the needle locking elements 80 and 82 may be forked, as shown in FIG. 2 and in the detail view of FIG. 3. One arm of the forked end 88 is positioned so as to engage each flattened area adjacent one end of the suturing needle, thereby locking the suturing needle in the needle receiver. Each needle locking element has an extended position wherein the working end engages the needle and a retracted position wherein the needle is released. In operating, with the needle engaging both needle receivers, one needle locking element is moved to engage the needle while the other is move to release the needle, thereby moving the needle from one arm to the other.

Alternative embodiments of the needle locking element may engage only one side of the needle and may have a curved or angled end.

Figure 12:
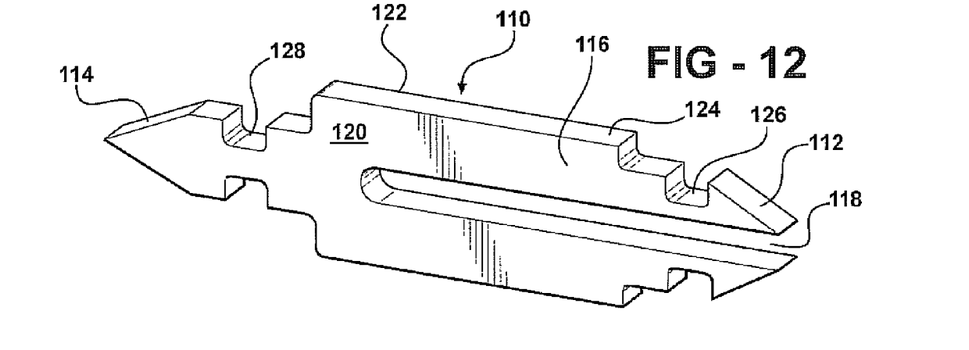
FIG. 12 is a perspective view of another embodiment of a suturing needle that may form part of the present invention.

Referring now to FIG. 12, an alternative embodiment of a suturing needle forming part of the present invention is generally shown at 110. The suturing needle 110 has a generally planar body having a first pointed end 112, a second pointed end 114 and a midportion 116 extending therebetween. The needle body has an elongated suturing receiving slot 118 extending from one of the pointed ends into the midportion 116 of the body. The needle body may be said to have first 120 and second 122 generally planar faces with a perimeter edge 124 between the faces. A notch 126 is defined in the perimeter edge adjacent the first pointed end 112 and a second notch 128 is defined in the perimeter edge adjacent the second pointed end 114. The suturing needle 110 may be used with the suturing device of the present invention, with the needle locking elements engaging the notches 126 and 128. As shown in FIG. 12, opposed notches may also be provided and may also be engaged by the ends of the needle locking elements. Alternative embodiments of either needle may have a suturing cavity that is not in the center, or may be bigger or smaller. The cavity may be a slit. As a further alternative, the opening 108 into the slot 106 of the needle 70 may be positioned closer to one end such that when that end is received in a needle receiver, the opening 108 is covered and the suturing material is trapped in the slot 106.

Referring again to FIG. 4, the needle receivers 60 and 62 each have a slot or opening defined in the housings 66 and 76 respectively. These slots are indicated at 130 and 132. The working ends of the needle locking elements are received in these slots to guide them into contact with the needles. A further guide housing, such as shown at 134, may be provided on the suturing arm in order to guide the needle locking elements. Other guides may be provided elsewhere, as needed.

Figure 9:
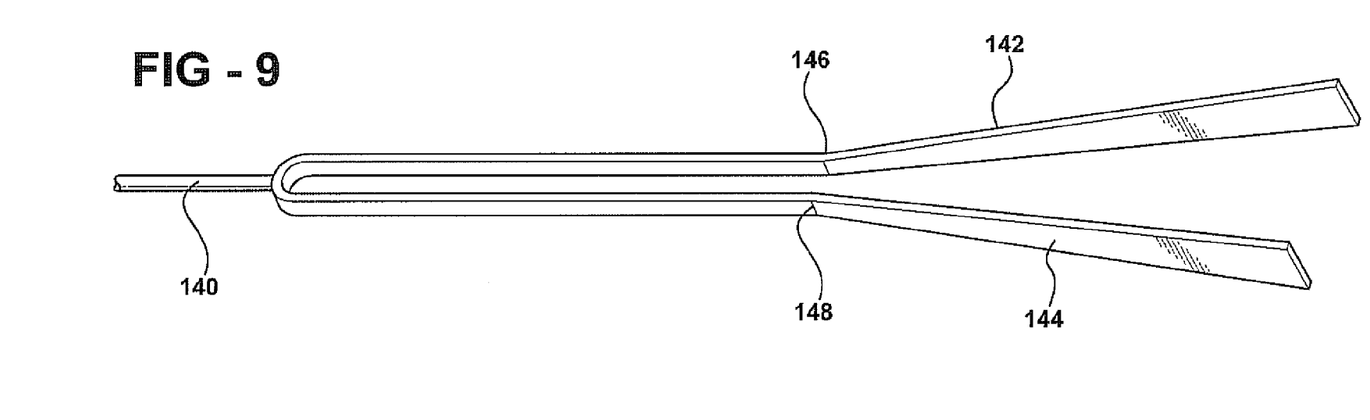
FIG. 9 is a side elevational view of suturing arms that form part of an alternative embodiment of the present invention.
Figure 10:
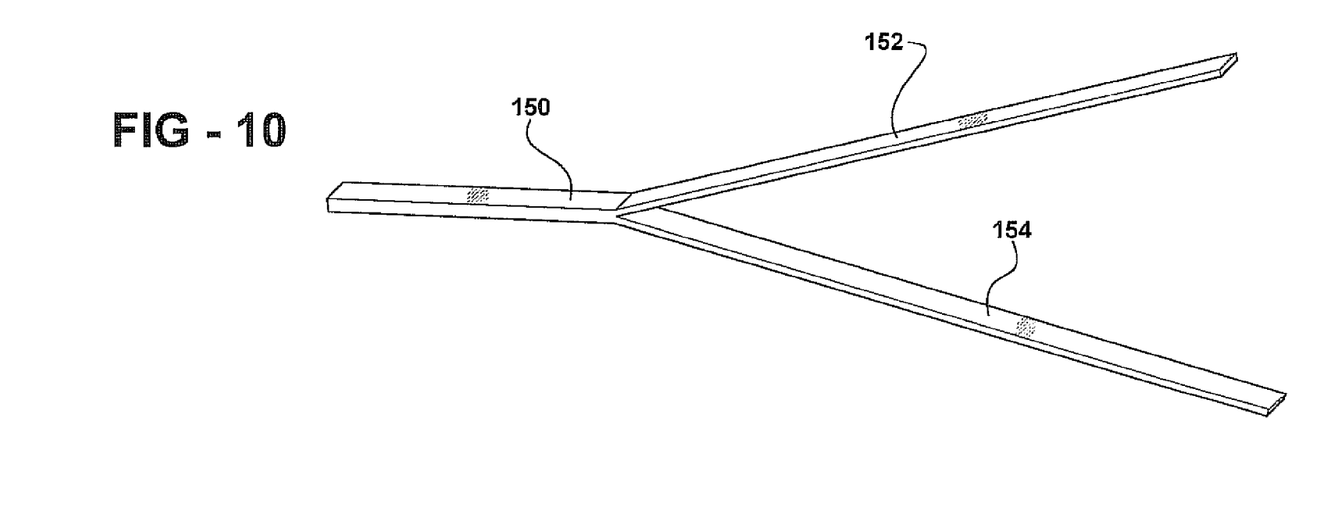
FIG. 10 is a side elevational view of suturing arms that form part of a further alternative embodiment of the present invention.

The suturing arms may take forms other than discussed thus far. Referring now to FIGS. 9 and 10, alternative embodiments of suturing assemblies will be discussed. In FIG. 9, a first alternative embodiment of a suturing assembly is shown. As with the earlier embodiment, the suturing assembly includes an elongated flexible base portion 140 and a pair of suturing arms 142 and 144 interconnected with the base portion 140. Unlike the earlier embodiment, the suturing arms are not designed to intertwine when flexed to the closed position. However the arms 142 and 144 do include transition regions 146 and 148 that come into contact when the arms are flexed to the closed position.

FIG. 10 illustrates a second alternative embodiment of a suturing assembly. Again, this design includes a base portion 150 and a pair of suturing arms 152 and 154. However, this design does not provide for a transition region where contact occurs between the arms. As such, stress levels are higher. As will be clear to those of skill in the art, the suturing assemblies would preferably include additional components, as were described for earlier embodiments, to provide a working suturing device.

As will be clear to those of skill in the art, proper operation of a suturing device according to the present invention requires manipulation of the suturing assembly, manipulation of the sheath and manipulation of the needle locking elements. A variety of control assemblies may be used to control these various elements, and the present invention is not limited to a particular one.

FIGS. 16-21 illustrate the use of the suturing device and suturing needle. In FIG. 16, the suturing needle 70 is loaded with suturing material 160 by positioning the suturing material in the slot 106. For ease of reference, the suturing arms of the suturing device illustrated in FIGS. 16-21 will be labeled as A and B. The Figures illustrate tying of the suturing material around a piece of tissue C, though it should be clear that the needle could be piercing the tissue instead.

Figure 17:
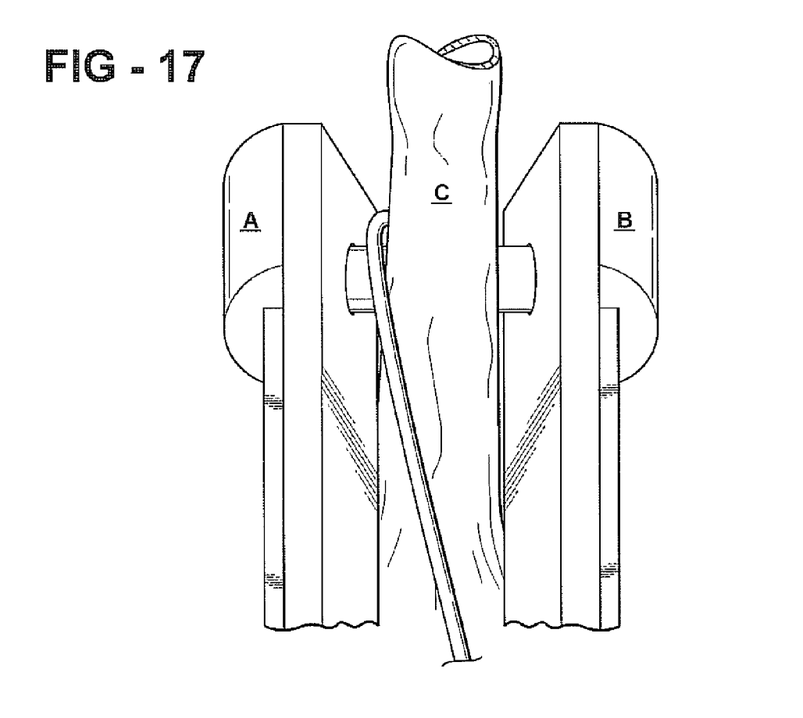
Figure 18:
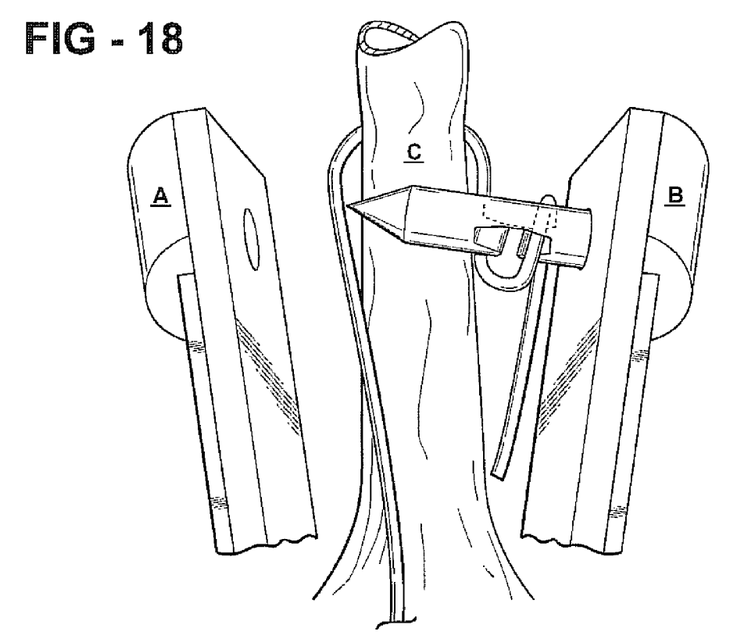
Figure 19:
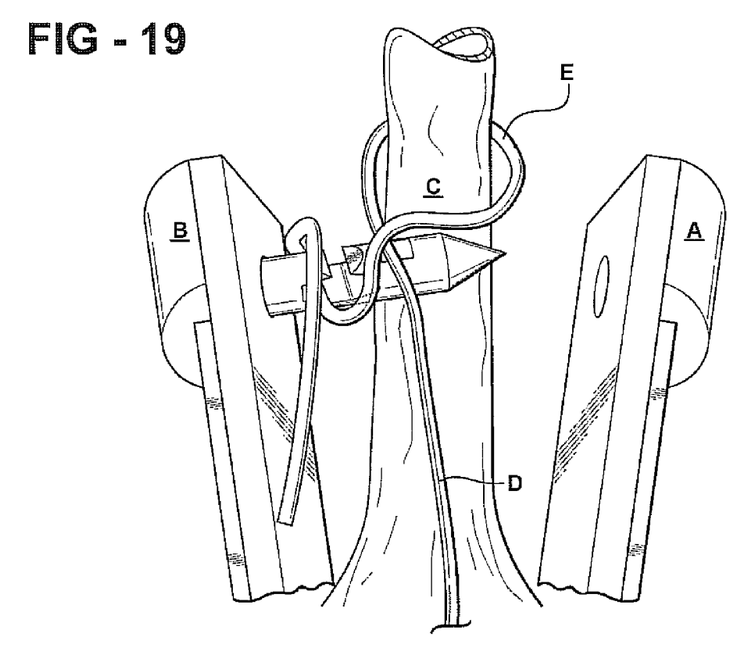
Figure 20:
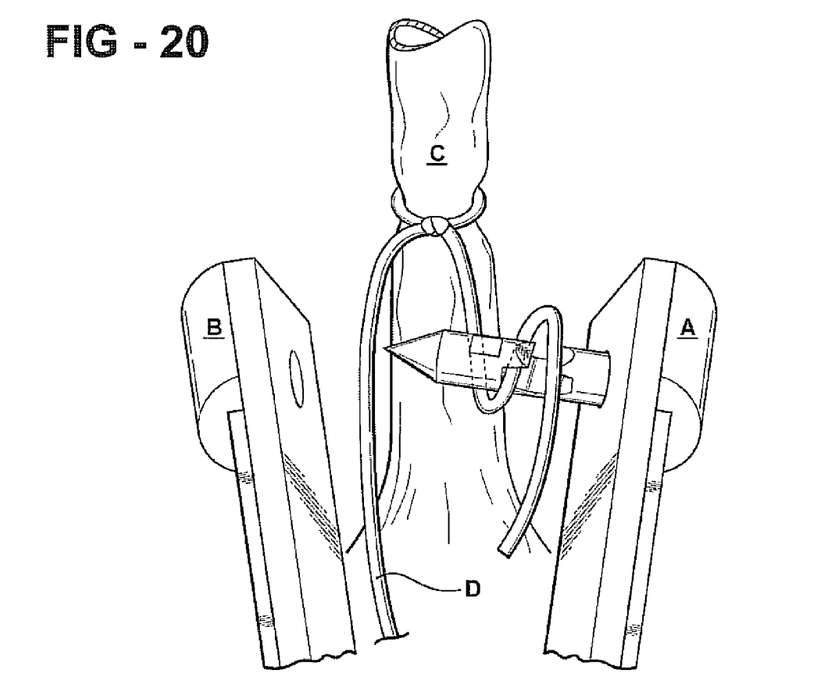
Figure 21:
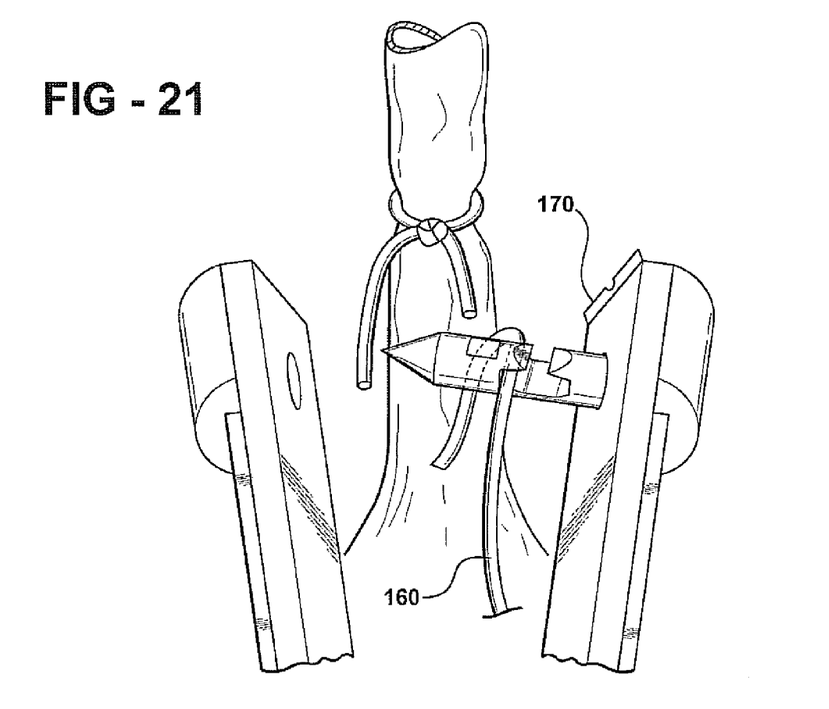

In FIG. 16, the needle 70 is retained by arm A. In this Figure, the opening 108 in the needle 70 is facing the rear. In FIG. 17, the arm A is used to pass the needle behind the tissue C and the suturing arms are moved to the closed position such that the needle engages arms A and B. The needle locking elements would be manipulated to release the needle from arm A and to engage the needle with arm B. In FIG. 18, the suturing arms are returned to the open position with the needle retained by arm B. In FIG. 19 the suturing arms A and B have been flipped such that arm B is now on the left so that the suturing material forms a loop around the tissue C. The suturing assembly may be rotated in the scope to rotate the arms. Though not shown, arm B is then used to pass the needle through the loop just formed (behind the downwardly extending portion of the suturing material labeled as D and through the loop labeled as E). In FIG. 20 the needle has been passed through the loop and is now engaged with Arm A, and the first part of the knot has been tightened around the tissue C. The process may be repeated to complete the knot, or the knot may be completed in other ways clear to those of skill in the art. FIG. 21 illustrates the completed knot and the suturing material has now been cut. According to further embodiments of the present invention, a cutting element, such as blade 170, a hook or other cutter, may be provided for severing the suturing material 160. The needle may then be reloaded in situ or depending on where the cut is made, the needle may remain loaded. Other cutting approaches may be used. As will be clear to those of skill in the art, multiple procedures may be performed, such as placing multiple sutures, without removing the device.

Some embodiments of the present invention also include a suture retaining means for retaining the free end of the suturing material when a knot is tied or tension is applied to the suturing material. The needle may be configured such that the suture material is compressed in the slit or cavity as the needle is locked into one of the jaws thus securing the free end and giving enough tension to tie the knot. Alternatively or additionally, the jaws may have small slits or openings through which the end of the suturing material is fed into the needle. These openings keep the suturing material in position for rethreading. The location of these openings can be above and/or below the slot for locking the needle.

As will be clear to those of skill in the art, a typical channel in an endoscope is not wide enough for a suturing device as shown herein to pass thru the working channel with a needle loaded. The length of the needle may be longer than the width of the channel. For situations where this is the case, several options may be used for loading the needle. In a first approach, the suturing device is passed through the working channel while the endoscope is outside the patient. The needle is then loaded, and the endoscope is inserted into the patient with the suturing device and needle in place. A needle cover may be provided for protecting the sharpened ends. Alternatively, the needle may be positioned between the closed jaws longitudinally (generally parallel to the jaws) so as to pass thru the working channel. Then, a variety of approaches may be used for repositioning the needle into a working position. In one approach, the jaws may have guide slots for guiding the needle into place. In another approach, the needle has attachments that are pulled to move it into position in one or both jaws. For example, caps may be provided on one or both ends of the needle, with a thread or filament attached to each cap. The thread or filament extends thru the hole in the jaw that will receive the needle. After the device is inserted thru the scope, the jaws are opened to release the needle. Then the thread or filament is drawn through the hole in the jaw until the needle is pulled into the hole. More tension may then be applied to the cap to remove it from the needle, leaving the needle in one of the jaws. In yet another approach, one end of the needle is received in a holder in one of the jaws and is then flexed into a generally longitudinal position for insertion of the device thru the scope. When the jaws open again, the tension is released and the needle returns to a more perpendicular position with respect to the jaw and may be repositioned or guided into the use position.

In yet a further approach to loading a needle, the needle may be dropped thru the working channel, possibly with suturing material or a filament attached. A second tool may be inserted into the working channel, or another channel in a two channel scope or additional scope. The second tool may be used to reposition the needle and either load it directly into the suturing device or position it in a holder on the end of the scope from which the suturing device can retrieve the needle.

As will be clear to those of skill in the art, the jaws and needle may be constructed in a variety of ways, and a variety of locking or engagement elements or structures may be provided. As will clear to those of skill in the art, the suturing device described herein may be constructed of a variety of materials. Examples include metals of various types, including titanium and stainless steel. Shape memory metal alloys may also be useful, as well as various other materials such as plastics or composite, though the high stress levels typical for this application suggest metals may be more suitable. Further, the entire suturing assembly may be formed of one material or the arms and other portions may be formed of different materials. In some embodiments, arms and possibly the base member may be a monolithic or unitarily formed piece. For example, referring back to FIG. 4, the arms 26 and 28 and the base 22 may be monolithicly formed. Alternatively, just the arms and the portion where the arms are joined may be monolithic.

As mentioned above, the suturing device according to the present invention may be constructed such that the suturing arms are part of a compliant mechanism such as by the arms being formed as distal ends of flexible members that extend through a sheath. While it is preferred that a moving sheath be used to bring the arms together, other approaches may also be used for articulating the arms. The arms may include hinges for pivoting relative to the remainder of the tool or may be flexible or use living hinges. Other variations will be clear to those of skill in the art. It is the following claims, including all equivalents, which define the scope of the invention.

We claim:

1. A suturing device for suturing with a suturing needle having a first end and a second end, the suturing device comprising:
   an elongated sheath having a working end for insertion through a working channel in an endoscope, the sheath having an inner passage defined through at least a portion of the sheath adjacent the working end;
   a suturing assembly comprising:
      an elongated flexible base member having a working end and a handle end;
      a first suturing arm having a proximal end interconnected with the working end of the elongated flexible base member and an opposite distal end, a first needle receiver disposed at the distal end of the first suturing arm;
      a second suturing arm having a proximal end interconnected with the working end of the elongated flexible base member and an opposite distal end, a second needle receiver disposed at the distal end of the second suturing arm;
      each suturing arm having a base segment and a working segment, the base segment extending from the proximal end to a transition region and the working segment extending from the transition region to the distal end;
      each of the needle receivers operable to receive and support a suturing needle independent of the other of the needle receivers;
      a first needle locking element interacting with the first needle receiver to selectively lock the suturing needle in the first needle receiver; and
      a second needle locking element interacting with the second needle receiver to selectively lock the suturing needle in the second needle receiver;
      the suturing arms being movable between an open position wherein the distal ends are spaced apart by a first distance and a closed position wherein the distal ends are spaced apart by a second distance less than the first distance, the base segments being generally parallel when the suturing arms are in the open position;
      wherein the first and second suturing arms are formed of a flexible and resilient material such that moving the suturing arms between the open and closed positions flexes the suturing arms, the suturing arms being biased towards the open position;
      the suturing assembly disposed through the inner passage of the sheath, the sheath being movable relative to the suturing assembly between a retracted position and an extended position, the sheath in the extended position engaging the suturing arms and urging the suturing arms towards the closed position.

2. The suturing device according to claim 1, wherein the suturing needle has a flattened portion adjacent each of the first end and another flattened portion adjacent the second end, the needle locking elements engaging the flattened portions to selectively lock the suturing needle in one of the needle receivers.

3. The suturing device according to claim 1, wherein the suturing needle has a pair of opposed flattened areas adjacent each of the first and second ends, the needle locking elements each having a forked end, the forked end engaging one of the pairs of opposed flattened areas to selectively lock the suturing needle in one of the needle receivers.

4. The suturing device according to claim 1, wherein each needle locking element comprises an elongated flexible base portion disposed adjacent the elongated flexible base member and a working portion disposed adjacent the suturing arms.

5. The suturing device according to claim 1, wherein the base segments of the suturing arms are generally disposed in the inner passage of the sheath when the sheath is in the retracted position, at least a portion of the working segments of the suturing arms being disposed in the inner passage of the sheath when the sheath is in the extended position.

6. The suturing device according to claim 5, wherein the working segments of the suturing arms are angled outwardly when the suturing arms are in the open position.

7. The suturing device according to claim 1, wherein the base segment of one of the suturing arms has a longitudinal slot disposed therethrough, the base segment of the other suturing arm being at least partially disposed in the slot when the suturing arms are flexed into the closed position.

8. The suturing device according to claim 1, wherein when the suturing arms are flexed from the open position to the closed position, the transition regions of the suturing arms are moved into contact, thereby reducing the stress in the flexible and resilient material forming the suturing arms.

9. The suturing device according to claim 1, wherein the elongated sheath has an outer diameter less than or equal to approximately 6 millimeters.

10. In combination, the suturing device according to claim 1 and a suturing needle, the suturing needle comprising:
   a needle body extending between a first pointed end and a second pointed end, the needle body having a flattened portion defined adjacent each of the first and second ends and a suture receiving slot defined in the needle body.

11. A suturing device for suturing with a suturing needle having a first end and a second end, the suturing device comprising:
   an elongated sheath having a working end for insertion through a working channel in an endoscope, the sheath having an inner passage defined through at least a portion of the sheath adjacent the working end;
   a suturing assembly comprising:
      an elongated flexible base member having a working end and a handle end;
      a first suturing arm having a proximal end interconnected with the working end of the elongated flexible base member and an opposite distal end, a first needle receiver disposed at the distal end of the first suturing arm;
      a second suturing arm having a proximal end interconnected with the working end of the elongated flexible base member and an opposite distal end, a second needle receiver disposed at the distal end of the second suturing arm;
      a first needle locking element interacting with the first needle receiver to selectively lock the suturing needle in the first needle receiver and a second needle locking element interacting with the second needle receiver to selectively lock the suturing needle in the second needle receiver;
      wherein each needle locking element comprises an elongated flexible base portion disposed adjacent the elongated flexible base member and a working portion disposed adjacent the suturing arms;
      wherein each needle locking element has a forked end disposed in one of the needle receivers;
      the suturing arms being movable between an open position wherein the distal ends are spaced apart by a first distance and a closed position wherein the distal ends are spaced apart by a second distance less than the first distance;

wherein the first and second suturing arms are formed of a flexible and resilient material such that moving the suturing arms between the open and closed positions flexes the suturing arms, the suturing arms being biased towards the open position;

the suturing assembly disposed through the inner passage of the sheath, the sheath being movable relative to the suturing assembly between a retracted position and an extended position, the sheath in the extended position engaging the suturing arms and urging the suturing arms towards the closed position.

12. The suturing device according to claim 11, wherein each suturing arm has a base segment and a working segment, the base segment extending from the proximal end to a transition region and the working segment extending from the transition region to the distal end, the base segments being generally parallel when the suturing arms are in the open position.

13. In combination, a suturing device and a suturing needle, comprising:
a suturing device having:
an elongated sheath having a working end for insertion through a working channel in an endoscope, the sheath having an inner passage defined through at least a portion of the sheath adjacent the working end; and
a suturing assembly having:
an elongated flexible base member having a working end and a handle end;
a first suturing arm having a proximal end interconnected with the working end of the elongated flexible base member and an opposite distal end, a first needle receiver disposed at the distal end of the first suturing arm;
a second suturing arm having a proximal end interconnected with the working end of the elongated flexible base member and an opposite distal end, a second needle receiver disposed at the distal end of the second suturing arm;
the suturing arms being movable between an open position wherein the distal ends are spaced apart by a first distance and a closed position wherein the distal ends are spaced apart by a second distance less than the first distance;
wherein the first and second suturing arms are formed of a flexible and resilient material such that moving the suturing arms between the open and closed positions flexes the suturing arms, the suturing arms being biased towards the open position;
the suturing assembly disposed through the inner passage of the sheath, the sheath being movable relative to the suturing assembly between a retracted position and an extended position, the sheath in the extended position engaging the suturing arms and urging the suturing arms towards the closed position; and
a suturing needle having a generally planar needle body having a first pointed end, an opposed second pointed end and a midportion extending therebetween, the needle body having an elongated suture receiving slot extending from one of the pointed ends into the midportion of the needle body.

14. The combination of claim 13, wherein the suturing needle body has a pair of generally planar faces with a perimeter edge interconnecting the planar faces, a notch being defined in the perimeter edge adjacent each of the pointed ends.

15. A method of suturing thru an endoscope, comprising providing endoscope with working channel defined therethrough;
providing a suturing needle having a first end and a second end;
providing a suturing device comprising:
an elongated sheath having a working end for insertion through the working channel in the endoscope, the sheath having an inner passage defined through at least a portion of the sheath adjacent the working end;
a suturing assembly comprising:
an elongated flexible base member having a working end and a handle end;
a first suturing arm having a proximal end interconnected with the working end of the elongated base member and an opposite distal end, a first needle receiver disposed at the distal end of the first suturing arm;
a second suturing arm having a proximal end interconnected with the working end of the elongated base member and an opposite distal end, a second needle receiver disposed at the distal end of the second suturing arm;
each suturing arm having a base segment and a working segment, the base segment extending from the proximal end to a transition region and the working segment extending from the transition region to the distal end;
each of the needle receivers operable to receive and support a suturing needle independent of the other of the needle receivers;
a first needle locking element interacting with the first needle receiver to selectively lock the suturing needle in the first needle receiver; and
a second needle locking element interacting with the second needle receiver to selectively lock the suturing needle in the second needle receiver;
the suturing arms being movable between an open position wherein the distal ends are spaced apart by a first distance and a closed position wherein the distal ends are spaced apart by a second distance less than the first distance, the base segments being generally parallel when the suturing arms are in the open position;
wherein the first and second suturing arms are formed of a flexible and resilient material such that moving the suturing arms between the open and closed positions flexes the suturing arms, the suturing arms being biased towards the open position;
the suturing assembly disposed through the inner passage of the sheath, the sheath being movable relative to the suturing assembly between a retracted position and an extended position, the sheath in the extended position engaging the suturing arms and urging the suturing arms towards the closed position;
disposing the suturing device thru the working channel of the endoscope;
positioning one end of the suturing needle in one of the needle receivers; and
suturing using the suturing needle and the suturing device.

* * * * *